(12) United States Patent
Dunlop (10) Patent No.: US 11,083,554 B2
(45) Date of Patent: Aug. 10, 2021

(54) MASK APPARATUS FOR VETERINARY APPLICATIONS

(71) Applicant: Colin Dunlop, East Ryde (AU)

(72) Inventor: Colin Dunlop, East Ryde (AU)

(73) Assignee: Colin Dunlop, East Ryde (AU)

( * ) Notice: Subject to any disclaimer, the term of this patent is extended or adjusted under 35 U.S.C. 154(b) by 1025 days.

(21) Appl. No.: 15/126,546

(22) PCT Filed: Mar. 31, 2015

(86) PCT No.: PCT/AU2015/000192
§ 371 (c)(1),
(2) Date: Sep. 15, 2016

(87) PCT Pub. No.: WO2015/149113
PCT Pub. Date: Oct. 8, 2015

(65) Prior Publication Data
US 2017/0079759 A1    Mar. 23, 2017

(30) Foreign Application Priority Data
Mar. 31, 2014 (AU) .................................. 2014901152

(51) Int. Cl.
*A61M 16/06* (2006.01)
*A61D 7/04* (2006.01)
*A62B 18/06* (2006.01)

(52) U.S. Cl.
CPC ............... *A61D 7/04* (2013.01); *A61M 16/06* (2013.01); *A61M 16/0622* (2014.02); *A61M 2250/00* (2013.01); *A62B 18/06* (2013.01)

(58) Field of Classification Search
CPC . A61D 7/04; A61M 2250/00; A61M 16/0622; A62B 18/06
See application file for complete search history.

(56) References Cited

U.S. PATENT DOCUMENTS

| 3,505,998 A | 4/1970 | Halstead et al. |
| 4,546,768 A | 10/1985 | Ferierabend |
| 4,582,055 A | 4/1986 | McDougal et al. |
| 5,299,531 A | 4/1994 | Dietz |

(Continued)

FOREIGN PATENT DOCUMENTS

| FR | 859106 A | * 12/1940 | ............. A62B 18/06 |
| GB | 611129 A | 10/1948 | |

OTHER PUBLICATIONS

International Search Report dated Apr. 29, 2015 in International Application No. PCT/AU2015/000192, filed Mar. 31, 2015.

(Continued)

*Primary Examiner* — Margaret M Luarca
(74) *Attorney, Agent, or Firm* — JCIP; Joseph G. Chu; Jeremey I. Maynard (57) ABSTRACT

The present invention relates to an improved mask apparatus for veterinary applications. The mask may be used for dogs in particular. Most prior art masks are conical. This leads to problems in comfort and effectiveness. The present mask has a cross sectional profile and an opening shaped similar to an animal's muzzle. It has a flat top and a flat bottom, slightly wider than the top, and rounded sides. It also extends backwardly from the top of the opening to the bottom of the opening, so as to comfortably cover the commissure of the animal's lips.

7 Claims, 9 Drawing Sheets

(56) References Cited

U.S. PATENT DOCUMENTS

| | | | | |
|---|---|---|---|---|
| 6,349,725 | B1* | 2/2002 | Perkins | A61D 7/04 128/206.21 |
| 2008/0066755 | A1* | 3/2008 | Janbakhsh | A61M 16/06 128/205.25 |
| 2009/0084378 | A1* | 4/2009 | Ichikawa | A61D 7/04 128/203.12 |
| 2009/0223517 | A1 | 9/2009 | Barney et al. | |
| 2012/0203125 | A1* | 8/2012 | Moran | A61D 7/04 600/532 |

OTHER PUBLICATIONS

International Preliminary Report on Patentability dated Jul. 18, 2016 in International Application No. PCT/AU2015/000192, filed Mar. 31, 2015.

* cited by examiner

MASK APPARATUS FOR VETERINARY APPLICATIONS

FIELD OF THE INVENTION

The present invention relates to an improved mask apparatus for veterinary application, and, particularly, but not exclusively, to a mask which can be used for treatment of animals such as dogs.

BACKGROUND OF THE INVENTION

In veterinary practice, it is known to treat animals using masks arranged to fit over the respiratory openings of the animal. The mask may be used to deliver therapy, medication, anaesthetic and for other treatments.

Current animal masks tend to be of similar form, generally conical in shape with a circular opening to receive the nose and mouth of the animal. The broad base of the cone forms the opening proximal to the animal's face and, the narrower part of the cone is distal to the base. The distal end of the cone may be flattened and may have a hole for the delivery of fluids into the mask. The mask may be connectable to a hose for the delivery of fluids via the hole.

These prior art masks usually incorporate a diaphragm at the circular opening to attempt to seal to the muzzle of the animal being treated.

These prior art masks tend to be quite uncomfortable for the animal to wear, and can be ill-fitting, causing stress and discomfort. For the delivery of drugs and for therapy which requires the mask to be worn for a period of time, it can be necessary to sedate the animal so that the mask will not be removed or damaged. This can be counter-productive to the treatment of the animal.

It is also very difficult to get an effective seal with this type of mask. In order to cover the commissure of the lips, the conical mask must be pushed tightly up the animal's snout, resulting in considerable discomfort. Also, even when pushed on firmly, sometimes the commissure extends out of the mask.

The volume of these conical masks can also be relatively large, leading to a relatively large dead space volume in the mask. This can lead to rebreathing of gases such as $CO_2$, which is not desirable.

Distress and discomfort is particularly marked in animals with dolicephalic faces, and where the conical opening of the mask must be pushed as far back as possible on the animal's muzzle to ensure that the mask extends over the commissure of the lips.

SUMMARY OF INVENTION

In accordance with a first aspect, the present invention provides a mask for respiratory treatment of an animal, comprising a housing having walls forming an enclosure arranged to receive an animal's muzzle, and forming an opening through which the muzzle is received, the profile of the opening being non-round, and relatively flat across the top of the enclosure to avoid obscuring vision of the animal wearing the mask, the walls of the mask proximate the opening being arranged to substantially conform to the shape of the muzzle of the animal and being of resilient material to hug the muzzle of an animal wearing the mask, wherein the profile of the opening is substantially oval with a flattened top and flattened bottom and the profile is wider at the bottom than at the top.

It has been found that, in at least an embodiment, the mask apparatus has the advantage that when it is being worn by an animal, such as a dog, it does not cause as much stress to the animal as the currently available conical masks.

In an embodiment, the cross-sectional profile of the housing transverse to the direction of receipt of the muzzle of an animal is generally of a similar profile for at least a portion of that housing extending from the opening, as the profile of the opening. It may taper inwardly from the opening.

In an embodiment, a portion of the walls of the mask proximate to the opening are of a soft material arranged to hug the muzzle of an animal wearing the mask. In an embodiment, the opening portion of the walls of the housing are formed of form fitting silicone.

In an embodiment, the walls of the mask proximate to the opening are formed as a cushion or curtain to form an internal seal against the muzzle of the mask in use. This cushion or curtain may be similar in form to the current design of human CPAP masks.

In an embodiment, the profile of the opening of the mask is arranged to extend backwardly from the top of the mask to the bottom of the mask in use, and the mask is arranged to cover over the commissure of the lips of the animal.

In an embodiment, an advantage of this profile is that the commissure of the lips of the animal is covered, without it being necessary to force the mask up the muzzle so that the top part confronts the eyes and causes discomfort. The top part of the mask, in use, sits away from the eyes so as to reduce interference with the animal's vision.

BRIEF DESCRIPTION OF THE FIGURES

Features and advantages of the present invention will become apparent from the following description of embodiments thereof, by way of example only, with reference to the accompanying drawings in which.

DETAILED DESCRIPTION OF EMBODIMENTS OF THE INVENTION

FIGS. 1, 2, 2a and 2b illustrate a prior art mask apparatus for use in veterinary applications. The mask apparatus is generally designated by reference numeral 1.

These types of mask apparatus are used for a number of applications in the veterinary area. For example, masks such as this can be used for anaesthesia, for oxygen therapy, for delivering medication such as asthma medication, delivering medication during recovery from anaesthesia, delivering oxygen during recovery or delivering any other fluids, for ventilation, and for many other applications.

Figures 1, 2A:
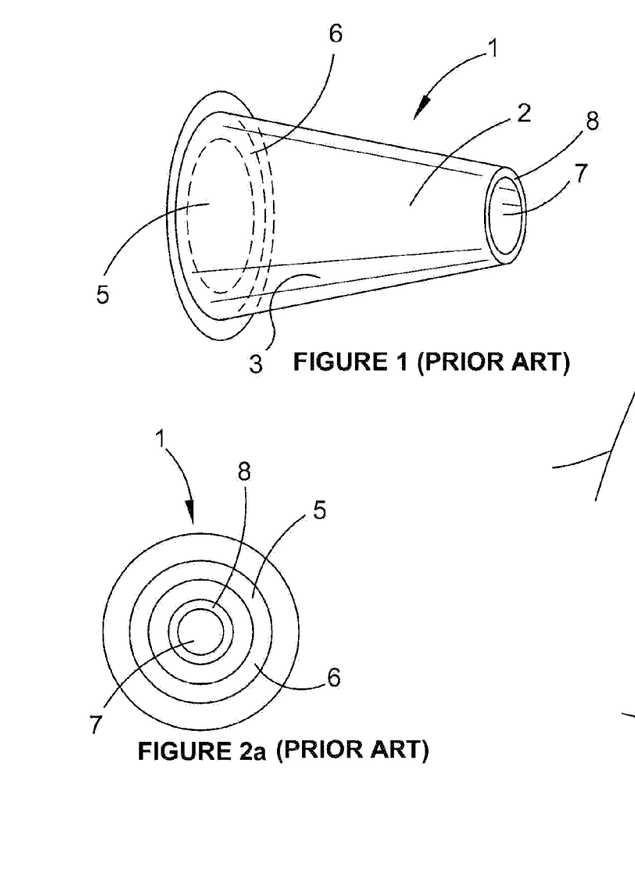
FIG. 1 is a perspective view of a prior art mask apparatus for an animal.
FIG. 2a is a view from the rear, or proximal end, of the mask apparatus of FIG. 1.
Figure 2:
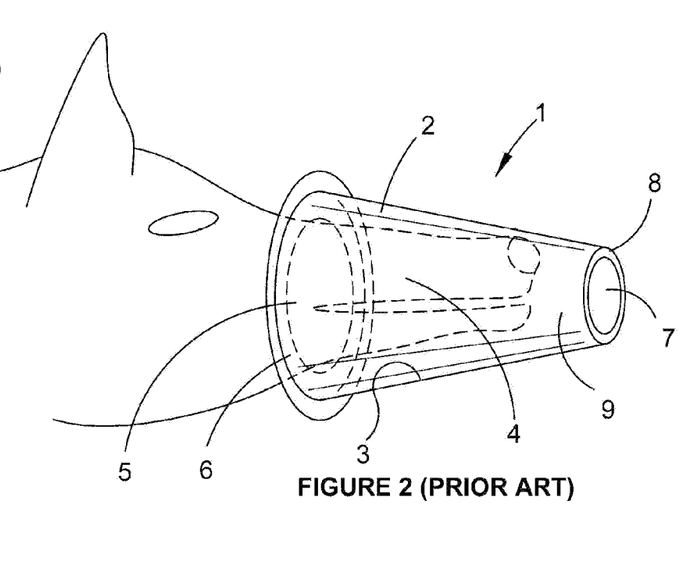
FIG. 2 is a further perspective view of the prior art mask apparatus of FIG. 1 shown in place with a diagrammatic representation of an animal's muzzle and head.

Referring to FIGS. 1 and 2, this prior art mask 1 comprises a mask housing having walls 2 which form an enclosure 3 for receiving an animal's muzzle 4 (FIG. 2). An opening 5, through which the muzzle 2 is received is formed by the walls 2. A resilient diaphragm 6, usually of rubber or other elastic material, is mounted about the opening 5. The muzzle 2 of the animal is placed through the opening 5 and the diaphragm 6 provides at least a partial seal between the muzzle and the mask, and also assists in retention of the mask on the animal.

The mask 1 has an opening 7 at the distal end 8 of the mask. Fluids, such as oxygen, can be introduced through this opening.

It can be seen that the mask apparatus 1 is generally conical in shape, extending from a wider base, at the proximally positioned opening 5 of the mask apparatus 1 to a narrower distal end 8. The opening 5 is circular in profile, and the mask apparatus 1 extends longitudinally from the proximal to the distal end in a narrowing cone shape with a circular transverse cross-section. FIG. 2a is a view from the proximal end of the mask apparatus 1 showing the circular cross-section substantially extending throughout the conical mask 1.

In practice, it is found that this style of mask causes discomfort to the animals. Animals will often try to remove the mask, leading to damage and non-satisfactory treatment. In order to prevent animals interfering with the mask, the animal patients are often sedated. Sedation can lead to other complications.

In order for the mask to cover the commissure, it must be pushed back a long way along the animal's face, as illustrated in FIG. 2. This leads to the top part of the base of the cone blocking the animal's view. This "confronting" of the animal's eyes causes considerable discomfort for the animal.

Even with the mask wall pushed back a long way along the animal's face, it may still be difficult to cover the commissure of the lips, so there can often be leakage around the opening 5 of the mask. The animal can breathe in ambient gases through a commissure that is not covered.

The diameter of the conical mask is often 30-50% above the minimum size that would fit the animal's nose tightly, because room must be made for the diaphragm. As discussed above, this causes obstruction to the animal's vision when pushed up to the eyes and causes discomfort. It also means the volume of the mask is relatively large, increasing dilution of additional fluids and increasing dead space, causing potential rebreathing of $CO^2$. For example, in FIG. 2, it can be seen that there is considerable dead space where illustrated by reference numeral 9.

Figure 2B:
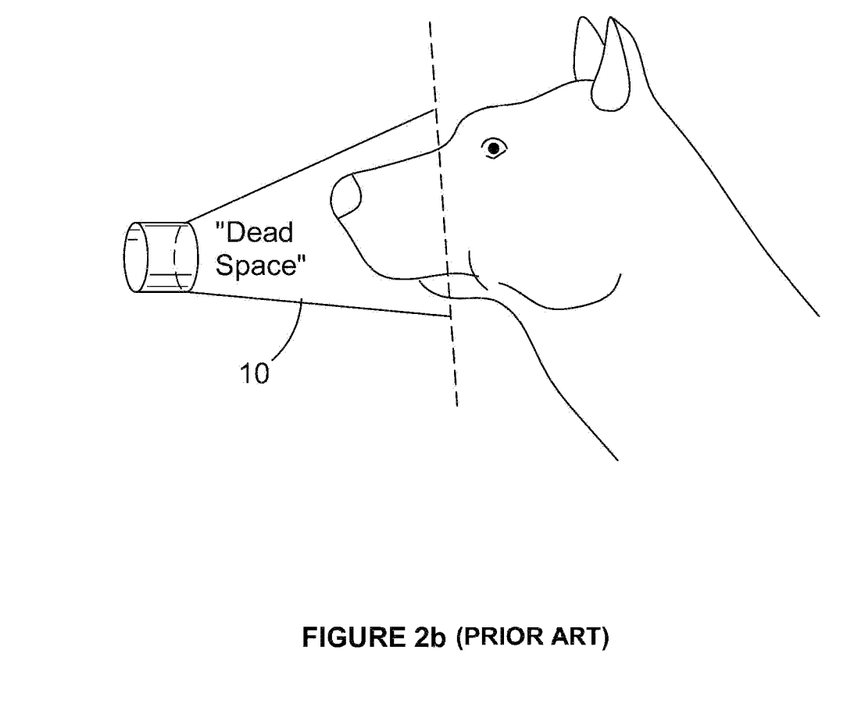
FIG. 2b is a side view of another prior art mask shown in place with a view of an animal's muzzle and head.

FIG. 2b shows another type of prior art mask 10, which in this embodiment does not have a diaphragm. This has to be pushed even more tightly on to the animal's head, causing further discomfort.

As well as these types of prior art mask causing considerable discomfort, and resulting in intolerance for long term wearing by the animal, it is also very difficult to get an effective seal. The lack of the effective seal prevents these types of masks being used for delivery of any form of positive pressure ventilation.

Figure 3:
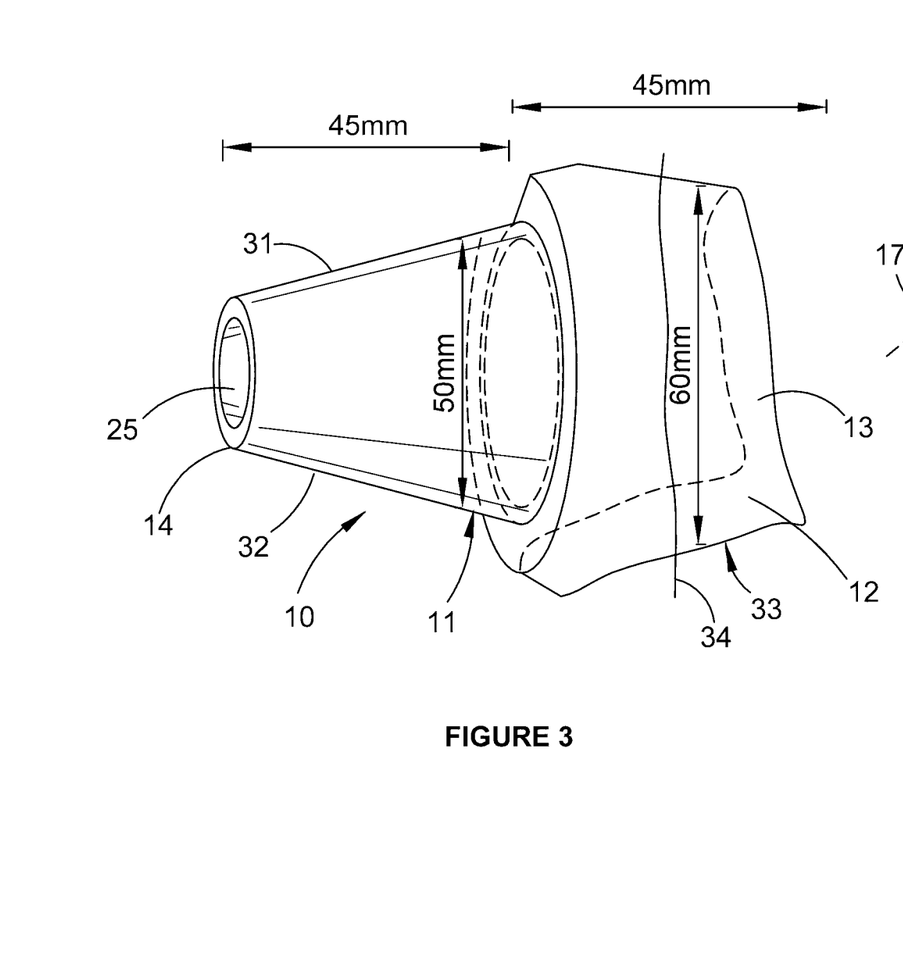
FIG. 3 is a perspective view from the side of a mask apparatus in accordance with an embodiment of the present invention.
Figure 4:
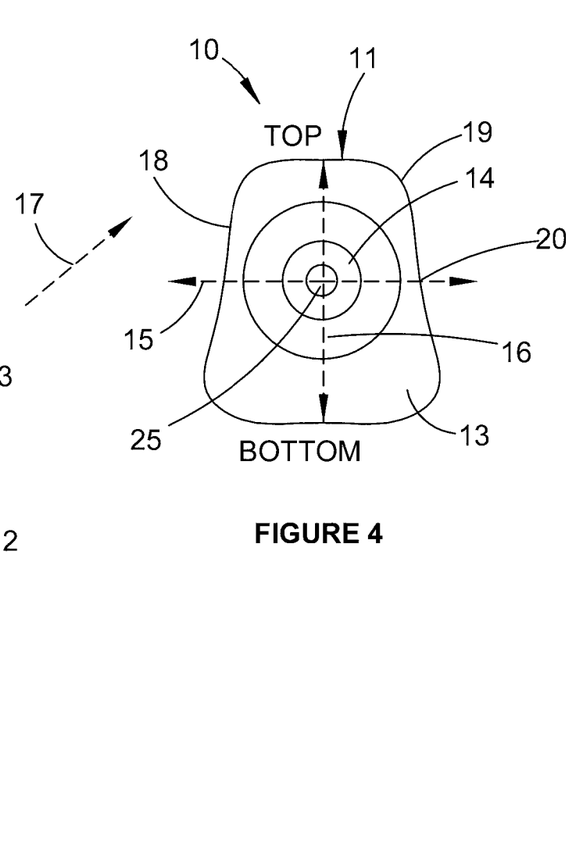
FIG. 4 is a view from the rear, or proximal end of the mask apparatus of the embodiment of FIG. 3.
Figure 5:
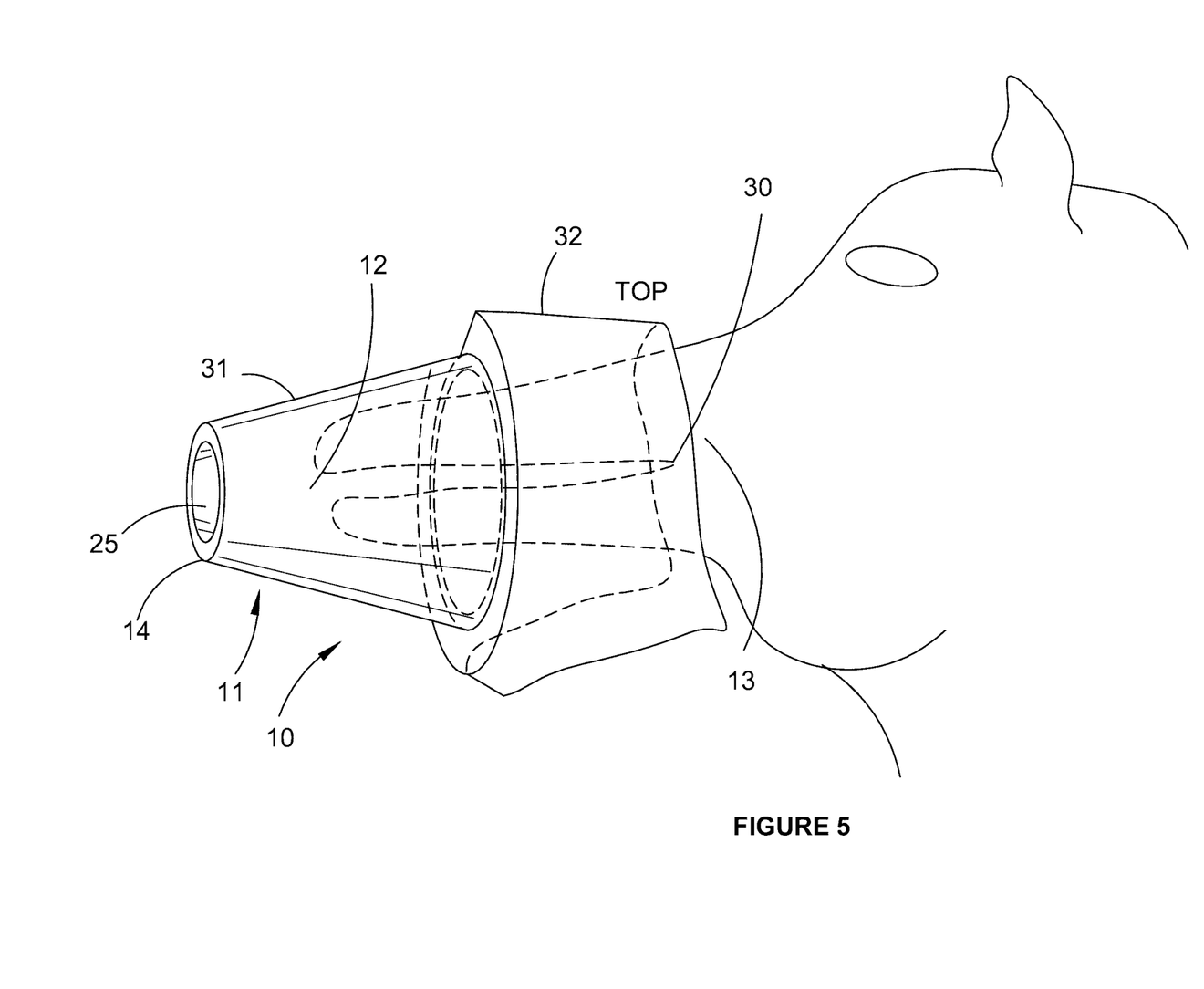
FIG. 5 is a perspective view from the side of the mask apparatus of the embodiment of FIG. 3, shown in place on a diagrammatic representation of a muzzle and head of an animal.

A mask apparatus in accordance with an embodiment of the present invention is illustrated in FIGS. 3 to 5.

Referring to the figures, the mask apparatus, generally designated by reference numeral 10 comprises a housing 11 having walls 12 which form the housing. The walls 12 also define an opening 13 through which the muzzle of an animal (see FIG. 5) may be received in operation.

The mask 10 has a distal end 14 which, in operation, is distal from the face of the animal. Referring to FIG. 4, the mask has a "TOP" and "BOTTOM" as indicated. In use, the Top of the mask apparatus 10 is positioned on the top of the animal's muzzle (see FIG. 5).

In relation to the Top and Bottom, the mask has a Lateral axis 20, extending across the mask from left to right as indicated in FIG. 4, an Upright axis 16 extending from the Bottom to the Top of the mask and a Longitudinal axis 17 represented by a broken line in FIG. 4 but in fact extending into the page from the crossover of the Lateral 20 and Upright axis 16 to the distal end 14 of the mask. The Left side of the mask is designated by reference numeral 18 and the Right side by reference numeral 19.

The opening 13 is defined by the walls 12 of the mask. As can be seen best in FIG. 4, the opening 13 is non-round in shape. Also, it can be seen that, in this embodiment, the Top is relatively flat across from Left side 18 to Right side 19.

It has been found, that when this mask is worn by animals, such as a dog, as shown in FIG. 5, it does not cause as much stress and discomfort as the prior art masks. In fact, in experiments, it has been found that animals such as dogs are happy to wear this apparatus without requiring sedation or even requiring a strap to secure the mask to their face. Of course, a strap can be provided for security.

The applicants believe that one of the problems with the prior art masks is that, because of its conical shape in particular, it tends to interfere with the animal's vision, because the base of the cone of the diaphragm tend to obstruct the animal's vision (see FIG. 2). Because of the flattened top 18 of the mask of this embodiment, it is believed that there is less interference and this may be one reason why the animal is more tolerant of this type of mask.

Note that at the distal end of the mask 14, there may be a hole 25 through which fluids can be passed for treatment and therapy of the animal. The hole 25 may be able to be connected to a conduit such as a tube for the passage of treatment fluids. This has a similar function to the hole 7 of the prior art mask of FIGS. 1 and 2.

As well as the flattened top, referring to FIG. 4 it can be seen that the profile of the mask, at transverse cross-section of the opening 13 is generally non-round. There is also a flattened Bottom, opposite the Top, and relatively flat sides 18, 19, forming a substantially rectangular or elongated oval shape. In this embodiment the Bottom is slightly wider than the Top. This shape is more appropriate to conform with the shape of an animal's muzzle such as dog, for example, than the round opening of the prior art conical masks. The longitudinal dimension of the mask can be relatively long, so that the mask can accommodate a dolicephalic snout. The mask may also be shaped to accommodate brachycefalic muzzles and may have a shorter longitudinal dimension for this.

In this embodiment, the same cross-sectional profile of the non-round opening extends longitudinally into the mask for at least a portion of the longitudinal dimension. In some embodiments it may taper inwardly.

Another feature of this mask apparatus design is illustrated in FIG. 5. The Bottom of the mask is set backwardly in the longitudinal direction from the Top of the opening the mask, so that the Top of the mask sits away from the eyes. The Bottom extending backwardly, enables the sides of the mask to extend over the commissure of the animal's mouth in use (the commissure is indicated by reference numeral 30 in FIG. 5).

A portion 31 of the mask (see FIG. 5 and FIG. 3) towards the proximal end of the mask apparatus is in conical form. The portion 32 towards the distal end, is, as discussed above, not conical, but shaped to accommodate the shape of the muzzle of the animal, in this case a dog. Note that the portion 31 of the mask need not be conical in shape but could be any other shape which is still able to receive the snout of the animal. Referring to FIG. 3, a portion 33 of the mask, extending between the opening 13 and the line 34 shown on FIG. 3, partway towards the distal end 14 from the opening 13, is made of resilient material which is able to flexibly conform with the muzzle of the animal where it receives the animal's muzzle, and to form a comfortable interface with the animal's muzzle, which can facilitate a seal. In an embodiment, this portion 33 is formed of a resilient silicone material. This has been found to be comfortable for the animal. The rest of the mask may be made of firmer plastics material in order to facilitate retention of shape than the portion 33. The use of this resilient portion of the mask apparatus, avoids the need for a diaphragm (such as used in the prior art masks).

In an embodiment, the portion 33 of the mask may also include an internal cushion type seal, similar in design to current human CPAP masks. The seal may be in the form of a cushion, or a curtain folded back on itself, to form a better seal against the animal's face and also to maintain comfort.

Embodiments of the present invention may be advantageously used for CPAP ventilatory support in conscious animals.

As discussed above, the portion 31 of the masks need not be conical. It could be shaped so as to reduce the dead space at the end of the mask. It could be blunt ended, for example. It could be any other shape.

Figure 8:
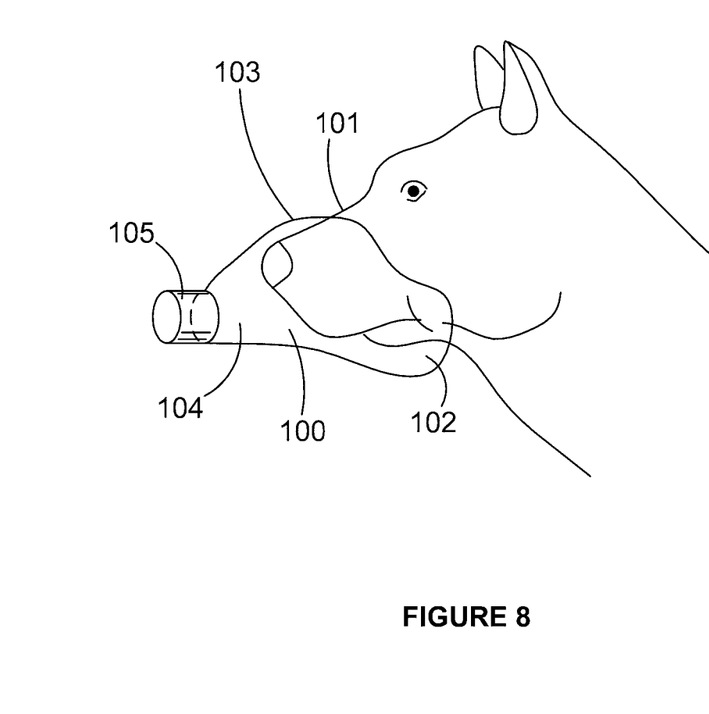
FIG. 8 is a perspective view from one side of a mask apparatus in accordance with a further embodiment of the present invention, shown positioned on a representation of an animal's muzzle and head.

FIG. 8 shows another embodiment of a mask apparatus in accordance with the present invention. The mask apparatus in this embodiment comprises walls 100 and an opening 101 arranged to receive the animal's muzzle. The bottom 102 of this mask extends back relatively more than in the previous embodiment. It easily covers the commissure of the animal's mouth. The top part 103 sits away from the eyes, as with the previous embodiment. The distal portion 104 of the mask apparatus is "blunter", so as to reduce dead space. A projection 105 is arranged to receive a tube for providing fluids.

Figure 6A:
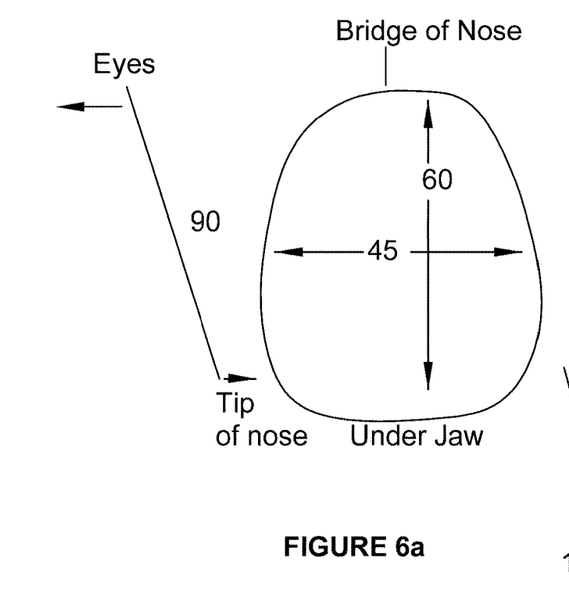
FIGS. 6a, 6b and 6c are diagrammatic views from the rear of mask apparatus in accordance with embodiments of the present invention, to illustrate dimensions of the apparatus for different sized animals.
Figures 6B, 6C:
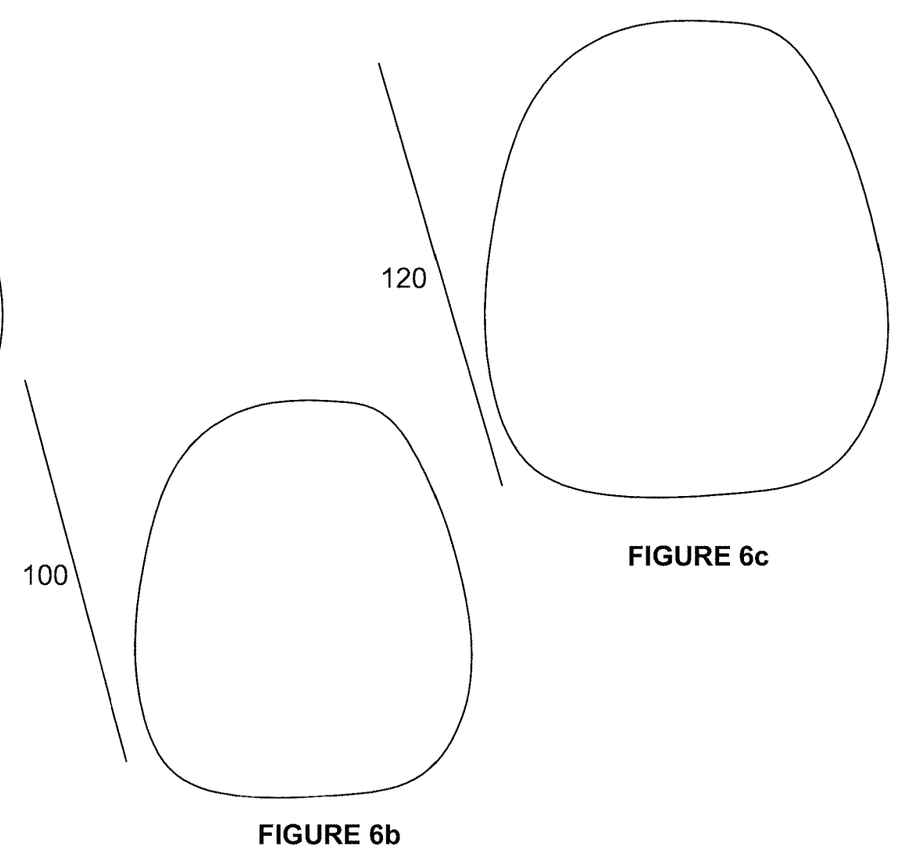

Masks in accordance with embodiments of the present invention may be of different dimensions to accommodate different sizes of animal muzzle. FIGS. 6a to 6c gives three examples of dimensioning of masks in accordance with the embodiment of FIGS. 3 to 5.

FIG. 6a, shows a diagram of the proximal end of the mask, showing the profile of the proximal end to show dimensions, in this case, 60 mm vertically and 45 mm horizontally. The mask may be 80 mm to 90 mm in a longitudinal direction. This may be useful to suit a small dog, such as a 12 to 15 kg animal. FIG. 3 shows other dimensions of this type of mask for a small dog. The dimensions are shown in millimeters.

FIG. 6b is for a medium dog, and the dimensions would include a longitudinal direction of in the order of 100 mm. Although this is a bigger mask, it can be seen that the dimensions are in the same proportion as with FIG. 6a.

FIG. 6c illustrates the profile of a mask which might be used for a big dog, such as a 25 to 35 kg animal. The mask and the longitudinal direction will be in the order of 120 mm long.

Figure 7:
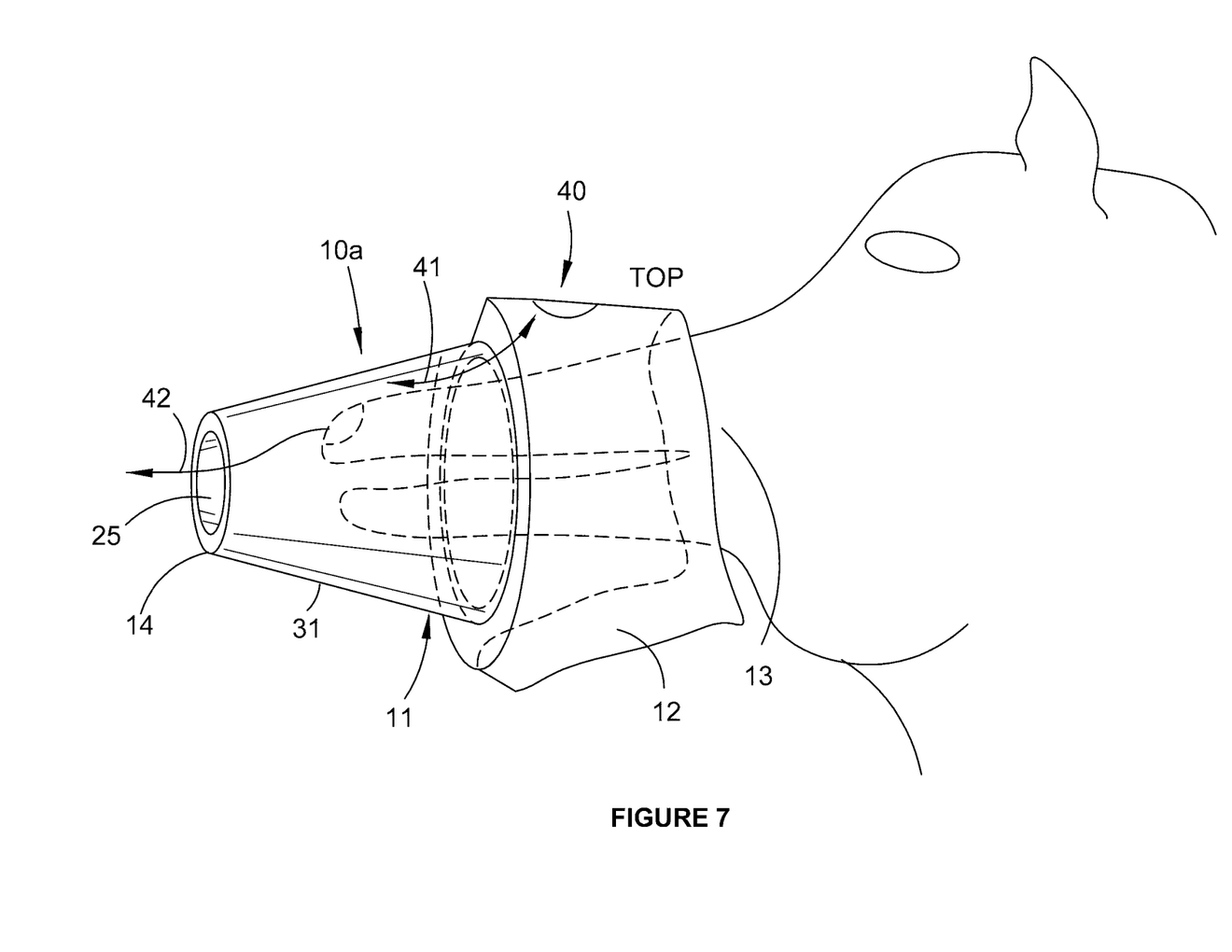
FIG. 7 is a perspective view from one side of a mask apparatus in accordance with a further embodiment of the present invention, shown positioned on a diagrammatic representation of an animal's muzzle and head.

FIG. 7 shows a further embodiment of a mask apparatus in accordance with the present invention. This further embodiment is generally indicated by reference numeral 10a. The same reference numerals have been allocated to components of mask apparatus 10a which are equivalent to components of the embodiment of FIGS. 3 to 5 and no further description will be given of these.

As well as a hole 25 in the distal end 14 of the mask apparatus of this embodiment, there is also a hole 40 in the top of the mask, over the animal's muzzle. In operation, fluids for treatment of the animal are introduced through the top hole 25 and exit through the hole 25. This reduces the "deadspace" in the mask and therefore facilitates treatment of the animal. This is an application of the applicant's earlier invention, as described in Australian Patent Application No. 2006252044, the contents of which are included herein by reference.

The hole 40 may be anywhere in the mask as long as it is close to the muzzle of the animal and results in the flow indicated by arrows 41 and 42, reducing the deadspace in the mask.

Figure 9:
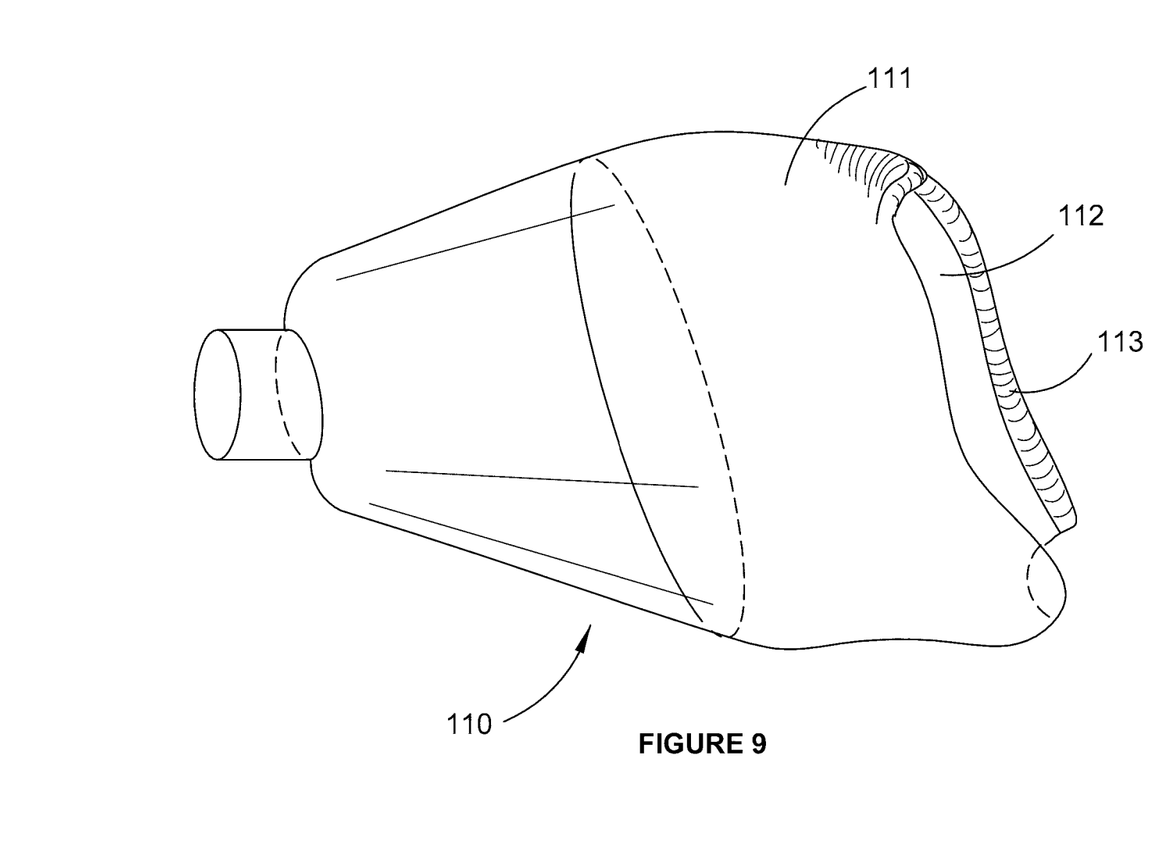
FIG. 9 is a perspective view from one side of a mask apparatus in accordance with a further embodiment of the present invention.
Figure 10:
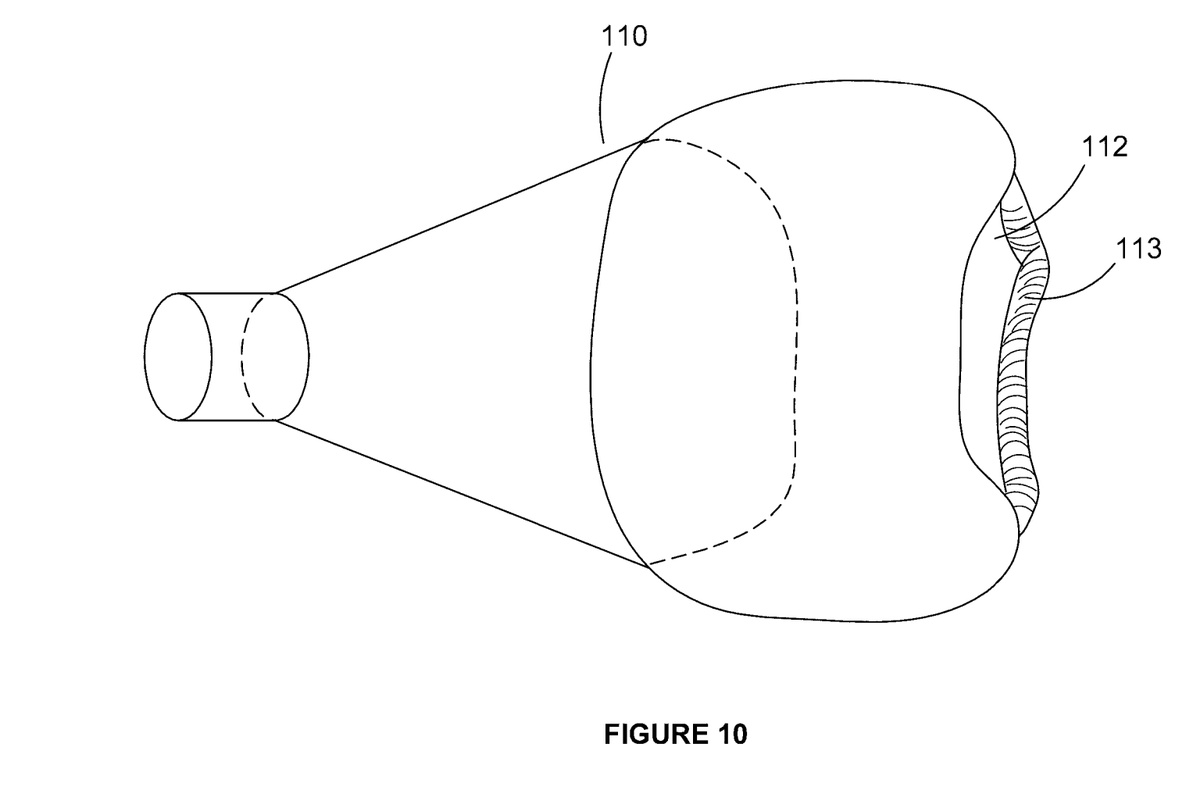
FIG. 10 is a top view of the mask apparatus of FIG. 9.

FIGS. 9 and 10 show further embodiment of a mask apparatus, generally designated by 110. The housing 111 has an opening 112. The opening is surrounded by a folded back flexible cushion 113, which in this embodiment is made of silicone. This may be similar in form to the cushion used in human CPAP masks.

Masks in accordance with embodiments of the present invention can be used for all the same treatments that prior art masks can be used for. These include the treatments discussed above, and also other therapeutic treatments, such as continuous positive airway pressure (CPAP) treatments.

It will be appreciated that the mask apparatus of the present invention is not limited to the dimensions shown and described with reference to FIG. 6, and other figures, and other dimensions could be used to accommodate different patient sizes The mask apparatus of the present invention is not limited for use with dogs, but could be used for other animals, particularly animals having snouts, including pigs, horses, and other animals.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A mask for respiratory treatment of an animal, comprising a housing having walls forming an enclosure arranged to receive an animal's muzzle, and forming an opening through which the muzzle is received, said housing having a distal end opposed to said opening which in operation is distal from the face of the animal, the profile of said opening being non-round and relatively flat across the top of the enclosure to avoid obscuring vision of the animal wearing the mask, wherein a portion of said housing has said walls extending longitudinally from said opening partway towards said distal end and being arranged to substantially conform to the shape of the muzzle of the animal and being of a resilient material to hug the muzzle of an animal wearing the mask, the profile of the opening is substantially oval with a flattened top and flattened bottom and the profile is wider at the bottom than at the top.

2. The mask in accordance with claim 1, wherein the resilient material is form-fitting silicone.

3. The mask in accordance with claim 2, wherein the profile of the opening of the mask being arranged to extend backwardly from the top of the mask to the bottom of the mask in use, and arranged to cover over the commissure of the lips of the animal.

4. The mask in accordance with claim 1, wherein the profile of the opening of the mask being arranged to extend backwardly from the top of the mask to the bottom of the mask in use, and arranged to cover over the commissure of the lips of the animal.

5. The mask in accordance with claim 1, further comprising an internal seal around the opening to improve sealing between the mask and the animal's muzzle.

6. The mask as claimed in claim 5, wherein the seal is in the form of a curtain folded back on itself to form a seal with the animal's muzzle under conditions of positive pressure within the mask.

7. The mask as claimed in claim 5, wherein the seal is in the form of a cushion.

* * * * *